United States Patent [19]

Hoshino et al.

[11] Patent Number: 4,892,876
[45] Date of Patent: Jan. 9, 1990

[54] METHOD FOR INHIBITING HIV AND AN PHARMACEUTICAL COMPOSITION THEREFOR

[75] Inventors: Hiroo Hoshino, Maebashi; Nobuyoshi Shimada, Tokyo, both of Japan

[73] Assignee: Nippon Kayaku Kabushiki Kaisha, Tokyo, Japan

[21] Appl. No.: 172,637

[22] Filed: Mar. 24, 1988

[30] Foreign Application Priority Data

Apr. 21, 1987 [JP]  Japan ................................ 62-98429

[51] Int. Cl.$^4$ ............................................. A61K 31/52
[52] U.S. Cl. ...................................... 514/265; 514/266
[58] Field of Search .................. 514/266, 265; 544/277

[56]  References Cited

U.S. PATENT DOCUMENTS 4,743,689  5/1988  Shimada et al. ..................... 544/277

OTHER PUBLICATIONS

Chem. Abst. 107:108900k, (1987), Hoshino et al.

Primary Examiner—Douglas W. Robinson
Assistant Examiner—Z. Fay
Attorney, Agent, or Firm—Henry C. Nields

[57]  ABSTRACT

A pharmaceutical composition for inhibiting Human Immunodeficiency Virus (HIV), which is characterized by comprising a compound represented by the formula (1)

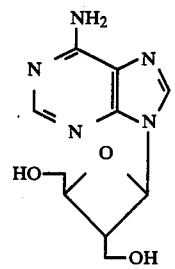

or a pharmaceutically acceptable salt thereof as an active ingredient.

2 Claims, No Drawings

METHOD FOR INHIBITING HIV AND AN PHARMACEUTICAL COMPOSITION THEREFOR

BACKGROUND OF THE INVENTION

It was discovered that Acquired Immuno-Deficiency Syndrome (AIDS) was a disease caused by Human Immunodeficiency Virus (HIV).

For example, LAV was isolated by Pasteur Institute and HTLV-III was isolated by National Institute of Health (NIH).

Azidothymidine (AZT) are used for treatment of AIDS. However, more effective and less side effective compound for treatment of AIDS are desired.

SUMMARY OF THE INVENTION

A pharmaceutical composition for inhibiting Human Immunodeficiency Virus (HIV) which comprises oxcetanocin represented by the formula (1)

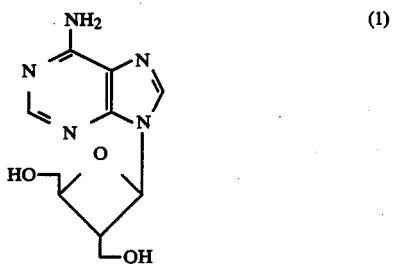

or an pharmaceutically acceptable salt thereof as an active ingredient, a method for inhibiting HIV in human cell which comprises applying the said oxcetanocin or an pharmaceutically acceptable salt thereof to the human cell. in an effective amount, and the use of oxcetanocin or a pharmaceutically acceptable salt for the manufacture of a medicament for inhibiting HIV in human cell. For treating patient with AIDS according to this invention, the oxcetanocin is administered to said patients in therapeutically effective amount.

DETAILED DESCRIPTION OF THE INVENTION

The inventors of the present invention have found that oxcetanocin represented by the formula

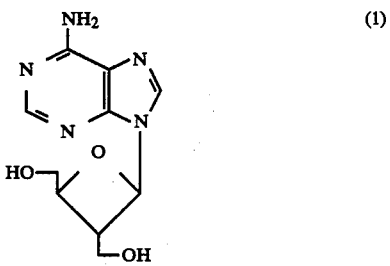

or a pharmaceutically acceptable salt thereof exhibits an antiviral effect on HIV and can be used as an antiviral agent against HIV, according to the results of their extensive investigation.

The present invention was accomplished by the above information.

A Compound represented by the formula (1), which is used in the present invention, is a known compound disclosed at the 1986 Annual Meeting of the Japanese Society of Agricultural Chemistry in Kyoto (see Program No. 3E-38, Summaries of Lectures of the Meeting, p.391). The compound (NK84-0218) of the present invention represented by the formula (1) is referred to as "the Compound" hereinafter.

The Compound forms salts with acids which may be pharmaceutically acceptable ones, for example, preferably, hydrochloric acid, sulfuric acid and phosphoric acid.

The Compound may be administered directly itself orally, but usually in admixture with excipients carriers or other adjuvants orally or as an injection or a suppository to patients with HIV. As the excipients and carriers a pharmaceutically acceptable one should be selected, and their type and composition are determined by the route and method of administration. For example, liquid carriers include water, alcohols, as well as animal, vegetable or synthetic oils such as soybean oil, peanut oil, sesame oil and mineral oil. Solid carriers include sugars such as maltose and sucrose, aminoacids, cellulose derivatives such as hydroxypropyl-cellulose, and salts of organic acids such as magnesium stearate. The following liquid carriers are generally preferred for injections: physiological saline, various buffer solutions, solution of sugars such as glucose, inositol and mannitol, and glycols such as ethylene glycol and polyethylene glycol. Alternatively, the Compound may be freeze-dried together with excipients such as sugars (e.g. inositol, mannitol, glucose, mannose, maltose, sucrose, etc.) and amino-acids (e.g. phenyl alanine etc.), and on administration, such freeze-dried composition may be dissolved in suitable solvents for injection, for example, a liquid for an intravenous injection such as sterilized water, physiological saline, glucose solution, electrolyte solution and amino-acids to be administered.

The content of the Compound in a pharmaceutical composition may be variable according to preparation, and usually ranges from 0.1 to 100 wt.%, preferably from 1 to 90 wt.%. For example, with injections, the favorable content of the Compound usually ranges from 0.1 to 5 wt. %. For oral administration, the form of tablets, capsules, powders, granules, liquids or dry syrups is used. With capsules, tablets, granules and powders, the content of the Compound is generally about 3 to 100 wt. %, preferably 5 to 90 wt. % and the rest is carriers.

The dosage is determined depending on the age, body weight and symptom of the patient as well as the purpose of treatment. The therapeutic dose generally ranges from 1 to 300 mg/kg.day for parenteral administration, and from 5 to 500 mg/kg.day for oral administration.

The Compound is slightly toxic, and every derivatives of it is characterized by low cumulative toxicity by repetitive administration. Any toxic sign has not been observed after 1 administration of dose of 800 mg/kg of the Compound for intraperitoneal administration in mice.

Formulation Examples of the present invention are shown below.

Formulation Example 1

30 parts by weight of the Compound (hydrochloride) (1) was mixed with purified water to make a total of 2,000 parts. The solution was passed through a millipore filter of GS type for sterilization purposes. 2 g of the filtrate was put into 10-ml vials and freeze-dried to prepare injections each containing 30 mg of the Compound (hydrochloride) per vial.

FORMULATION EXAMPLE 2

GRANULES

An intimate mixture of 50 parts by weight of the Compound (hydrochloride), 600 parts of lactose, 330 parts of crystalline cellulose and 20 parts of hydroxypropyl cellulose was compacted with a compacting machine of rolling type (Roller Compactor ®), and ground into particles which were sieved to provide granules of a size between 16 and 60 mesh.

FORMULATION EXAMPLE 3

TABLETS 30 parts by weight of the Compound (hydrochloride), 120 parts of crystalline lactose, 147 parts of crystalline cellulose and 3 parts of magnesium stearate were processed with a V-type pellectizing machine to produce tablets each weighing 300 mg.

Next, the antiviral activity against AIDS of the Compound will be illustrated in detail by Experimental Example.

EXPERIMENTAL EXAMPLE

ANTI-HIV (HUMAN IMMUNODEFICIENCY VIRUS) activity

About 50,000 cells/ml of MT-4 cell was introduced into a tray having 24 holes. Further, 100 ul of a solution containing a predetermined quantity of oxcetanocin was added, and then it was cultured in a 5% (v/v) carbon dioxide gas incubator at 37° C. for 2 hours. Subsequently, $10^3$ to $1.0^4$ infective units of HIV were added and cultured for 5 days. Then, the inhibition of cytopathic effect was observed microscopically.

Further, a part of the cultured fluid was applied to a slide glass and fixed with acetone, and development of virus antigen was examined by the fluorescent antibody technique. A serum of an AIDS patients was used as the primary antibody of the fluorescent antibody technique, and FITC-labelled anti-human IgG was used as its secondary antibody.

Cytotoxic effect of oxcetanocin on MT-4 cell was examined without adding virus according to the above technique.

| Activity of Oxcetanocin on HIV | | | |
|---|---|---|---|
| Concentration (ug/ml) | Inhibition of cytopathic effect | Development of virus antigen | Cytotoxicity |
| 30 | ++ | + | — |
| 10 | + | ++~+++ | — |
| 0 | — | +++ | — |

Effect

As is apparent from the above-mentioned experimental results, the Compound is not cytotoxic at concentration of 30 ug/ml, predominantly inhibitory to cytopathic effect, and very suppressive to development of virus antigens.

We claim:

1. A method for inhibiting HIV in human cell in vivo which comprises applying oxetanocin represented by the formula (1)

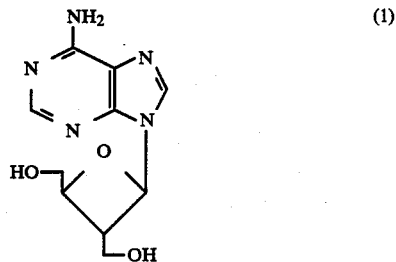

or a pharmaceutically acceptable salt thereof to the human cell in a therapeutically effective amount.

2. A method for inhibiting HIV in human cell in vitro which comprises applying oxetanocin represented by the formula (1)

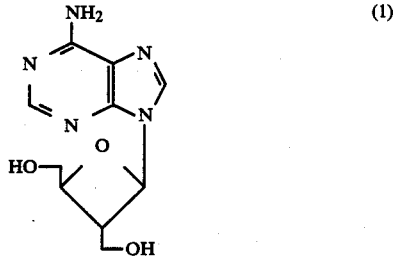

or a pharmaceutically acceptable salt thereof to the human cell in a therapeutically effective amount.

* * * * *